United States Patent [19]

Sano et al.

[11] Patent Number: 5,328,985

[45] Date of Patent: Jul. 12, 1994

[54] RECOMBINANT STREPTAVIDIN-PROTEIN CHIMERAS USEFUL FOR CONJUGATION OF MOLECULES IN THE IMMUNE SYSTEM

[75] Inventors: Takeshi Sano, Albany; Charles R. Cantor, Berkeley, both of Calif.

[73] Assignee: The Regents of the University of California, Oakland, Calif.

[21] Appl. No.: 729,460

[22] Filed: Jul. 12, 1991

[51] Int. Cl.$^5$ .................. C07K 3/00; C07H 21/04; A61K 35/14; C12Q 1/00

[52] U.S. Cl. .................. 530/350; 530/391.1; 530/391.5; 536/22.1; 536/23.1; 536/23.2; 536/23.4; 536/23.7; 435/7.1; 435/252.3; 435/69.1; 435/320.1

[58] Field of Search .............. 530/350, 387; 435/69.1, 435/7.1, 320.1, 252.3; 536/22.1, 23.1, 23.2, 23.4, 23.7

[56] References Cited

U.S. PATENT DOCUMENTS

| | | | |
|---|---|---|---|
| 4,478,914 | 10/1984 | Giese | 428/407 |
| 4,839,293 | 6/1989 | Cantor et al. | 435/320 |
| 5,100,788 | 3/1992 | Löfdahl | 435/69.7 |
| 5,109,124 | 4/1992 | Ramachandran | 536/27 |
| 5,168,049 | 12/1992 | Meade | 435/69.1 |

FOREIGN PATENT DOCUMENTS

| | | |
|---|---|---|
| 135532 | of 0000 | European Pat. Off. . |
| 900773.7 | 2/1984 | European Pat. Off. . |
| 8501901 | 10/1985 | PCT Int'l Appl. . |
| WO8602077 | 4/1986 | PCT Int'l Appl. . |
| WO8802776 | 4/1988 | PCT Int'l Appl. . |
| WO8809344 | 12/1988 | PCT Int'l Appl. . |
| WO8909393 | 10/1989 | PCT Int'l Appl. . |

OTHER PUBLICATIONS

Argarana, C. E.; Konty, I. D.; Birken, S.; Axel, R.; Cantor, C. R., Molecular Cloning and Nucleotide Sequence of the Streptavidin Gene, *Nuc. Acids. Res.*, 14:1871–1887 (1986).

Sano, T., Cantor, C. R. Expression of a Cloned Streptavidin Gene in *Escherichia Coli*, Proc. Nat. Acad. Sci., 87:142–146 (1990).

Sano, T., Cantor, C. R. Expression Vectors for Streptavidin-containing Chimeric Proteins, Bioch. Biophys. Res. Comm., 176:571–577 (1991).

Surolia, A., Pain, D., Khan, M. I., Protein A: Nature's Universal Antibody, Trends Biol. Sci., pp. 74–76, (Feb. 1982).

Sano, T., Cantor, C. R., Cooperative Biotin Binding by Streptavidin, J. Biol. Chem., 265:3369–3373 (1990).

Bayer, E. A., Ben-Hur H., Wichek, M., Isolation and Properties of Streptavidin, Meth. Enzym., 184:80–89 (1990).

Green, M. N., Avidin and Streptavidin, Meth. Enzym., 184:51–67 (1990).

Lowenadler, B.; Nilsson, B.; Abrahmsen, L.; Moks, T.; Ljunggvist, L.; Holmgren, E.; Paleus, S.; Josephson, S.; Philipson, L.; Uhlen, M. Production of Specific Antibodies Against Protein A Fusion Proteins, E.M.B.O.J 5:2393–2398 (1986).

Sano, Takeshi and Cantor, Charles, *A Streptavidin–Protein A Chimera that Allows One-Step Production of a Variety of Specific Antibody Conjugates*, Biotechnology, vol. 9, pp. 1378–1391, (Dec. 1991).

*Primary Examiner*—Robert A. Wax
*Assistant Examiner*—Hyosuk Kim
*Attorney, Agent, or Firm*—Hana Dolezalova

[57] ABSTRACT

A novel recombinant streptavidin-protein A chimeric protein which allows conjugation of antibody molecules with biological materials. The chimeric protein is efficiently expressed in *Escherichia coli* and is purified by simple procedures. The purified chimetic protein can bind one biotin molecule and one to two immunoglobulin molecules per subunit.

1 Claim, 9 Drawing Sheets

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: plasmid DNA ( i i i ) HYPOTHETICAL: no ( i v ) ANTI-SENSE: no ( v ) FRAGMENT TYPE:

( v i ) ORIGINAL SOURCE:
        ( A ) ORGANISM: E. coli
        ( I ) ORGANELLE: plasmid pUC8

( v i i ) IMMEDIATE SOURCE:
        ( B ) CLONE: plasmids pTSA-18F and pTSA-19F
        485.03- 41b - PATENT ( x i ) SEQUENCE DESCRIPTION: SEQ ID NO: 1:

```
AAG  GTG  AAT  TCG  AGC  TCG  GTA  CCC  GGG  GAT  CCT    33
Lys  Val  Asn  Ser  Ser  Ser  Val  Pro  Gly  Asp  Pro
1                   5                        10

CTA  GAG  TCG  ACC  TGC  AGG  CAT  GCA  AGC  TTC  GAT    66
Leu  Glu  Ser  Thr  Cys  Arg  His  Ala  Ser  Phe  Asp
15                       20
```

RECOMBINANT STREPTAVIDIN-PROTEIN CHIMERAS USEFUL FOR CONJUGATION OF MOLECULES IN THE IMMUNE SYSTEM

The invention was supported by research grant CA39782 from the National Cancer Institute, National Institutes of Health. The United States Government may have certain rights in this invention.

BACKGROUND OF THE INVENTION

Field of Invention

This invention concerns a novel recombinant streptavidin-Protein A chimeric protein which allows specific conjugation or labeling of antibody molecules with biological materials or, conversely, labeling such materials with antibodies. The chimeric protein can be efficiently expressed in *Escherichia coli* and can be purified by simple procedures. The chimeric protein purified to homogeneity has full biotin binding ability, and binds one to two immunoglobulin molecules per subunit.

RELATED DISCLOSURES

Streptavidin is a protein very closely related to a protein avidin which provides a very stable noncovalent complex with vitamin D-biotin. Avidin itself is a very highly specialized protein that is only rarely expressed. Streptavidin, on the other hand, is readily expressed in a species Streptomyces, in *Streptomyces avidinii*. Streptavidin specifically binds a water soluble vitamin D-biotin (vitamin H). Similarly to avidin, it also binds rapidly and almost irreversibly and with a remarkably high affinity to any molecule which contains an unhindered biotin. Streptavidin, contrary to avidin, is carbohydrate free and thus more suitable, for example, for X-ray crystallographic studies because of its homogenous molecular structure, or for various other detection techniques because of reduced non-specific binding. The comparative properties of avidins and streptavidins are described *Methods in Enzymology*, 184:51 (1990). Isolation and properties of natural streptavidin, as well as its preparation are described in Ibid., at page 80.

Expression of a cloned streptavidin gene in *Escherichia Coli* is described in *Proc. Natl. Acad. Sci.*, 87:142 (1990) and the cooperativity of the biotin binding of streptavidin is described in *J. Biol. Chem.*, 265:3369 (1990).

Staphylococcal protein, Protein A (Sp A) is a cell wall constituent of *Staphylococcus aureus*. Protein A specifically interacts with immunoglobulins, mainly IgG from mammalian species. Because of this property, Protein A has gained an increasing importance as a tool in both quantitative and qualitative immunological techniques. Binding of immunoglobulins of various species and types is described in *J. Immunol. Meth.*, 62:1 (1983).

Protein A was used, for example, for coating erythrocytes in order to quantify the number of rosetted lymphocytes bearing surface IgG and to follow the synthesis of IgG. Protein A has also been labeled with fluorescein isothiocyanate to demonstrate membrane-associated antigens, to detect B-cell alloantigens, to follow cell surface phenomena such as patching or capping, to label porcine lymphocytes and to enumerate T and B lymphocytes in human peripheral blood. $^{125}$I-labeled Protein A is useful for detection of antibody on the cell surface. Ferritin coupled covalently to Protein A has been used as an immunocytochemical reagent, and a native Protein A as a non-covalent bridging agent between specific antibodies and antiferritin has been used for electron microscopy. Protein A coupled to horseradish peroxidase was used to see membrane (T and B lymphocyte) and viral antigens on cells infected with measles, vesicular stomatitis, herpes or visna virus. Gold-labelled Protein A can be used in electron microscopy to label antigen-antibody sites on lymphocytes, platelets, virus-transformed rat kidney cells, vesicular stomatitis virus and red cells previously coated with specific antibody, and also for the ultrastructural localization of antigens in different tissues. As described in *J. Histochem. Cytochem.*, 28:55 (1980), Protein A labelled with FITC molecules and gold particles has been used in both light and electron microscope immunocytochemistry.

The $^{125}$I-labelled Protein A assay meets the demand of a rapid and sensitive serological test for attachment of antibody to cell-surface antigens during the selection and cloning of hybridomas. It has been successfully used to estimate alloantigens, tumor antigens, and to test a considerable number of cell types including sarcomas, melanomas, carcinomas, fibroblasts, lymphomas, thymocytes, erythrocytes, and to detect antibodies to L$_2$C leukemia cells as described in *J. Immunol. Meth.*, 31:201 (1979). $^{125}$I-labelled Protein A was used to follow the production of specific IgM anti-tumor antibodies, and for decorating immune precipitates (*Proc. Nat'l Acad. Sci.*, 76:3116 (1979)) when the particular component could not be selectively labelled. As seen in *J. Immunol. Meth.*, 24:269 (1978), $^{125}$I-Protein A is also useful as a general tracer in radioimmunoassay technique successfully applied to antigens such as human chorionic gonadotropin, human IgM and IgE, goat IgG, and haptens such as methotrexate, leucovorin and 5-methyl-tetrahydrofolate. $^{125}$I-Protein A is also useful in a solid phase antibody binding inhibition test and in a non-competitive radioimmunoassay for human IgG anti-iodination of tyrosine residues.

Work employing highly purified human T and B lymphocyte cells shows that insoluble Protein A markedly stimulates B cells but does not affect T cells and the stimulation of B cells is independent of the presence of T cells. Protein A has also been shown to induce the synthesis of polyclonal antibodies in B lymphocytes of human and mouse origin, and is probably a T cell-regulated polyclonal activator of human B cells. *Scand. J. Immunol.*, 10:593 (1979).

Various properties of avidin and streptavidin vis-a-vis biotin were studied and described. For example, the property of avidin to form strong, stable avidin-biotin complexes have been described in the U.S. Pat. No. 4,478,914 and utilized in a process for applying multiple layers of a protein and a ligand extender to a surface of the multiple-layer system. U.S. Pat. No. 4,478,914 concerns a process of preparing multiple layer system for modification of surface properties of biological, nonbiological, organic or inorganic surface. The multiple layer system is repetitive and employs a protein such as avidin, a ligand material such as biotin and an extender, a material to which one or more ligands are attached. The described process was used to increase of the extent of attachment of an enzyme, antibody, coenzyme, etc. Nowhere does this patent suggest the use of a streptavidin-Protein A chimeric protein as a way to conjugate antibody material with biological materials containing biotin.

This reference has no bearing on or similarity to the chimeric proteins of the current invention other than that it contains a combination of biotin with avidin as alternate layers of the disclosed system.

PCT US/89/01152 application describes luminescent chimeric proteins which combine a photoprotein with a second protein which may be avidin or streptavidin. An essential part of the new chimeric protein is a photoprotein. The photoprotein may be linked to another protein having specific affinities, such as the proteins avidin, streptavidin or Protein A. Chimeric photoproteins containing molecules of this invention are extremely sensitive ($10^{-18}$ moles) and are therefore useful for detection of various specific antibodies.

The only similarity between this application and the current invention is that two proteins bearing certain properties are joined in an expressed new chimeric protein which encompasses properties of both original proteins. The most essential portion of the protein of PCT/US89/01152 application has photoprotein properties and thus confers luminescence on the new protein.

In the current invention, two proteins, Protein A and streptavidin with distinct binding properties are joined and expressed as a new streptavidin-Protein A chimeric protein. Protein A specifically binds to Fc domain of an immunoglobulin G (IgG). Streptavidin binds specifically to biotin. The new chimeric protein binds thus to both immunoglobulins and biotin and may therefore easily conjugate or label any biological material containing biotin with antibodies.

The disclosure in the PCT US88/01737 concerns targeted multi-functional proteins which have specific binding affinity for pre-selected antigens. These proteins are expressed from recombinant DNA as a single polypeptide chain containing plural regions. One of the regions has a structure similar to an antibody binding site and possesses an affinity for a pre-selected antigenic determinant. The other region has a separate function and may be biologically active. These targeted multi-functional proteins comprise constant or variable domains (V). Each variable domain is made of three hypervariable regions called "complementarity determining regions" (CDR) interposed with framework regions (FR). The hypervariable regions are responsible for the binding specificity of individual antibodies and account for a diversity of binding of antibodies as protein class.

The proteins according to the invention described in PCT US/88/01737 are designed at the DNA level. The DNA encodes an optimal leader sequence used to promote expression in procaryotes which has a built-in cleavage site recognizable by, for example, a cleavage enzyme which removes the leader after expression. The DNA then encodes V domains comprising CDRs and FRs, a linker between the two domains, a spacer and an effector protein. After expression, folding and cleavage of the leader, a bifunctional protein is produced having a binding region whose specificity is determined by the CDRs and by the peptide-linked independently functional effector region.

Using the complex method described above, the invention of this PCT application thus provides a family of recombinant proteins which are expressed from a single piece of DNA and which have the capacity to bind specifically with the predetermined antigenic determinant. This invention provides an array of self-targeted proteins each of which has a specific function. While the above cited PCT reference mentions protein A as a possible effector protein, its combination with streptavidin and biotin molecules which would give specific properties of that combination to the multifunctional protein of the reference is nowhere suggested or described.

The chimeric proteins designed and expressed according to the current invention are molecules possessing certain specific properties inherently connected with the two proteins, i.e. streptavidin and Protein A, of which the resulting chimeric protein is composed. The present invention is based on the specific behavior of Protein A which binds to Fc domain of an immunoglobulin G molecule with high affinity and on the properties of streptavidin which binds specifically to water soluble vitamin D-biotin. Properties of both proteins, combined, provide a new recombinant streptavidin-Protein A derivative which possesses full biotin-binding ability, which binds one or two IgG molecules per subunit, which can be easily incorporated into various biological materials and which are able to introduce antibody molecules into biological materials, conjugate such antibodies with biological materials, remove such antibodies from these materials, or detect the presence of the antibodies in such materials. The binding affinity of the chimeric protein for both biotin and IgG can be used to provide antibody molecules with additional biological recognition capability.

SUMMARY

One aspect of the current invention is a recombinant streptavidin-Protein A chimeric protein having two independent biological recognition specificities.

Another aspect of the current invention is an expression system for the cloned streptavidin gene which expresses streptavidin in *Escherichia coli* and allows expression of a streptavidin-Protein A chimeric protein.

Another aspect of the current invention is the construction of an expression vector pTSAPA-2 for a streptavidin-Protein A chimeric protein by inserting the Protein A gene encoded in the plasmid pRIT11 into an expression vector for streptavidin-containing chimeric proteins pTSA-18F.

Another aspect of the current invention is an amino acid composition of the streptavidin-Protein A chimeric protein encoded in pTSAPA-2.

Another aspect of the current invention is the expression of gene fusion of streptavidin with Protein A using T7 expression system.

Still another aspect of the current invention is a method of purification of the streptavidin-Protein A chimeric protein.

Another aspect of the current invention is the method for conjugation of antibody-containing streptavidin-Protein A chimeric protein with various biological materials.

Still another aspect of the current invention is an incorporation of the antibody-containing streptavidin-Protein A chimeric protein into biological materials containing biotin.

Yet another aspect of the current invention is the method for introducing antibody materials into the tissue, removing the antibody from the tissue or labeling the tissue with antibody.

DETAILED DESCRIPTION OF THE INVENTION

Figure 1:
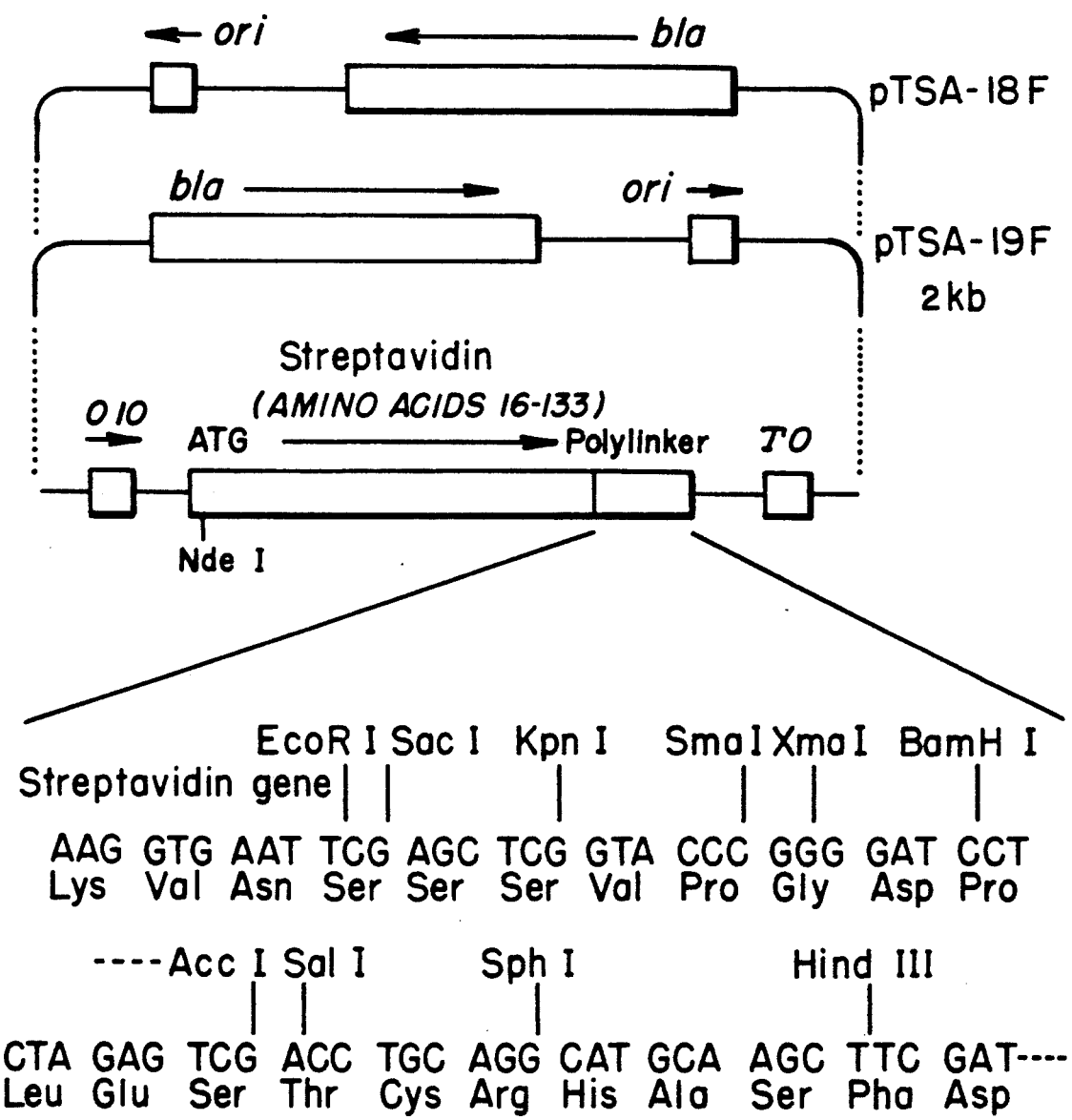
FIG. 1 represents expression vectors pTSA-18F and pTSA-19F for streptavidin-containing chimeric proteins.

This invention concerns recombinant streptavidin-Protein A chimeric proteins and their antibody-containing derivatives. Specifically, this invention provides a recombinant streptavidin-Protein A chimeric protein having two biological recognition specificities. A gene fusion of streptavidin with Protein A encoding two immunoglobulin G (IgG)-binding domains was efficiently expressed in *Escherichia coli* and the expressed chimeric protein was purified to homogeneity by simple procedures. The purified chimeric protein can bind one biotin molecule per subunit and has thus full biotin-binding ability and can also bind one or more immunoglobulin molecules per subunit. With the specific and tight binding affinity of the streptavidin-Protein A chimeric protein both for immunoglobulins and biotin, any biological material containing biotin may be conjugated and/or labeled with immunoglobulin molecules and/or such molecules may be incorporated into any biological material which contains biotin.

Two biological recognition specificities of the streptavidin-Protein A chimeric protein of the current invention are conferred on that protein by streptavidin which specifically binds biotin with extremely high affinity and by Protein A which binds various antibodies, preferably IgG with high affinity. Since biotin can be easily incorporated into various biological substances, the streptavidin-biotin system offers an avenue by which the second system, namely Protein A-bound antibody, such as human or other mammalian IgG, $IgG_1$, $IgG_2$, $IgG_3$, $IgG_4$, IgM, IgA, SIg A or IgE, can be incorporated into, conjugated with or used for labeling of biological materials.

Streptavidin

Streptavidin is a protein closely related to avidin. Like avidin, streptavidin was found to bind rapidly and almost irreversibly to any molecule containing biotin with specific affinity $Kd \approx 10^{-15}M$. The strong and specific binding affinity of streptavidin for biotin and the potential ability of biotin to be easily incorporated into various biological substances have made the streptavidin-biotin system a useful biological tool for detection and characterization of various biological materials. Cloning and sequencing of the streptavidin gene was described in *Nucleic Acids Res.*, 14:1871 (1986). Streptavidin coded for a sequence of 159 amino acids, some 30 residues longer than avidin. Streptavidin contains no carbohydrate and has a slightly acidic isoelectric point which minimizes nonspecific adsorption to most of the biological materials, such as nucleic acids.

Streptavidin can be isolated from culture broth of *Streptomyces avidinii* according to methods described in *Arch. Biochem. Biophys.*, 106:1 (1964) and lately in *Methods in Enzymology*, 184:51 and 80 (1990). Streptavidin has a molecular mass of about 66 kDa and consists of four identical subunits. Each subunit, which is 16.5 kDa in size, is capable of binding one biotin molecule. However, such an intact molecule is easily proteolyzed to about 13.5 kDa, which is so-called "core streptavidin". In addition, the native tetramer tends to form higher order oligomers. All of these molecules have biotin-binding ability.

The thermal stability of streptavidin is remarkable. In the presence of SDS, streptavidin begins to dissociate into its subunit monomers and dimers only at temperatures above 60° C. when all protein is dissociated into subunits having apparent $M_r$ 14,000.

Efficient expression of a cloned streptavidin gene in *Escherichia coli* using T7 expression system is described in *Proc. Natl. Acad. Sci.*, 87:142 (1990). The establishment of the expression system allowed the design and preparation of streptavidin-containing chimeric proteins. *J. Biol. Chem.*, 265:3369 (1990) describes the cooperativity of the biotin binding of streptavidin.

Protein A

Protein A (SPA) is known and considered to be nature's universal anti-antibody. Protein A is present and can be isolated from the cell wall of most strains of *Staphyloccus aureus*. One of the best producers is strain Cowan I (ATCC-12598; NCTC-8530) which contains about 1.7% Protein A by weight and its cell wall contains 6.7% Protein A. Protein A is mainly found covalently linked to the peptidoglycan of the cell wall and a small portion of it (~8%) is secreted into the growth medium. Lysostaphin digestion of the bacteria followed by ion-exchange, gel filtration and affinity chromatography on IgG-Sepharose yields relatively pure Protein A. However, certain methicillin-resistant strains of *S. aureaus* synthesize Protein A quite normally but do not incorporate it into the cell wall. Although there is a good correlation between Protein A production and deoxyribonuclease and coagulase activity, there is no correlation between the absence or presence of Protein A and any pathogenic property.

Protein A consists of a single polypeptide chain of molecular weight 42,000 and contains little or no carbohydrate. Its high frictional ratio of 2.1–2.2 and intrinsic viscosity suggest that it has a highly asymmetric and markedly extended structure. Its isoelectric point is 4.85–5.15. The native molecule is composed of about 50% of α-helices, and is very stable over a wide pH range from 0.99 to 11.8. Amino acid analysis shows that the protein has a C-terminal lysine and a blocked N-terminal amino acid. It contains no tryptophan nor half cystine residues but has four chemically equivalent tyrosine residues which are fully exposed on the surface. These tyrosine residues can be modified by tetranitromethane and acetylimidazole and are probably responsible for the protein's biological activity.

Protein A is characterized by its ability to interact, to some degree, with the IgG of almost all mammals, and in some species with IgA, IgM and other Ig molecules, such as IgE or SIgA as well. Protein A does not bind avian IgG and gives only a weak reaction with ruminant IgG. However, the ability of goat and sheep IgG antibodies to bind Protein A is enhanced markedly by immune binding to immobilized antigen or hapten. Within a species, the interaction may be restricted to certain subgroups of IgG, e.g., human $IgG_1$, $IgG_2$ and $IgG_4$ bind to Protein A with high percentage of reactivity, but not $IgG_3$.

When Protein A binds to the Fc portion of IgG, the Fab region is not affected. It is probable that both the CH2 and CH3 domains of rabbit IgG are involved in forming the binding site for Protein A. Protein A consists of six regions—five highly homologous domains are Fc-binding whereas the sixth, C-terminal domain, is bound to the cell wall and does not bind Fc. In the Protein A molecule, only two sites for IgG are active and their affinity for the Fc-region is identical (TIBS, 75 (February 1982)). Four combining sites on Protein A with different affinities for native IgG and antigen-modulated IgG have also been reported in *Immunochemistry*, 15:639 (1978).

Protein A is chemotactic, blocks heat-labile as well as heat-stable opsonins, activates or inhibits complement fixation depending on the dose and produces a hypersensitive reaction when injected into some animals and man, but produces no marked symptoms in the mouse. The in vitro release of leukocyte lysozyme and histamine by staphylococcal antigens and injury to rabbit and human platelets mediated by Protein A have been reported. The interaction of Protein A with the Fc-region of IgG exposes sugar moieties which are essential for complement binding. However, neither NMR nor proton relaxation enhancement studies show evidence of a large conformational change in the Fc fragment when it binds to Protein A. It has been suggested in TIBS, 75 (February 1982) that the binding sites for Protein A and $C_1$ on the Fc-region are close to each other or even that they are identical.

The specific IgG-binding affinity of Protein A, with a host species and subclass specific manner, allows a variety of immunological applications, such as purification of antibodies, specific detection and separation of antibodies dependent on their host species and subclasses, and detection of various biological molecules through their antibodies. Antibodies are one of the most useful biological tools because of their specificity and variation. To enhance the capabilities of antibodies and allow them to be easily conjugated or labelled with other biological materials by providing additional biological recognition capability, a streptavidin-Protein A chimeric protein of this invention was designed.

Chemically cross-linked streptavidin-Protein A complex is usually heterogenous in quality. Particularly, number of cross-links, shape of the molecule, biotin-binding ability, IgG-binding ability, and the quality of the material is affected by the cross-linking conditions. In contrast, the streptavidin-Protein A chimeric protein according to this invention has completely homogenous quality, which allows the extensive use and application of the product. Furthermore, the cost to produce such molecules can be substantially reduced.

The natural Protein A contains five IgG-binding domains, but can usually bind only two IgG molecules probably because of structural hindrance. In contrast, a recombinant Protein A molecule containing two IgG-binding domains can bind two IgG molecules. (Eur. J. Biochem. 186; 557 (1989).) Therefore, the truncated Protein A moiety containing two IgG-binding domains in the streptavidin-Protein A chimeric protein of this invention is expected to bind two IgG molecules if there is no structural hindrance.

Construction of Expression Vector

Figure 2:
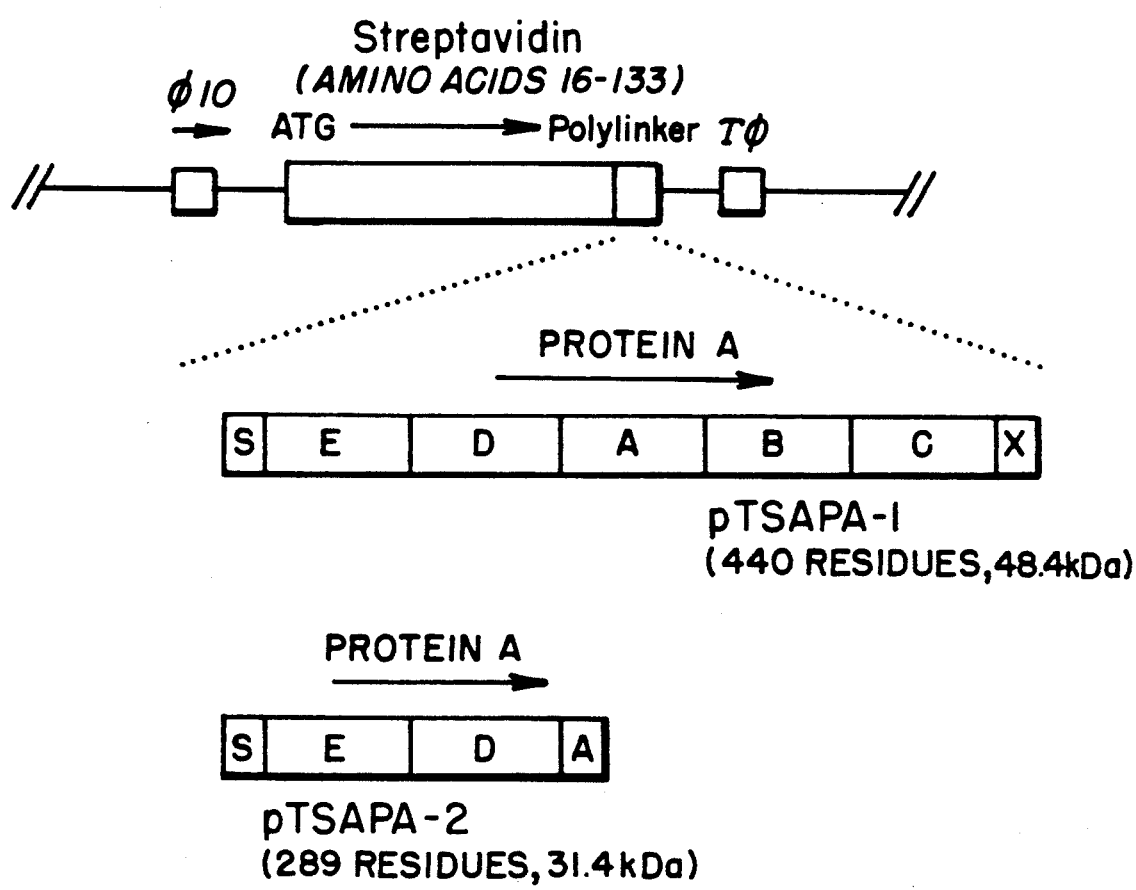
FIG. 2 represents two expression vectors pTSAPA-1 and pTSAPA-2 constructed for streptavidin-Protein A chimeric proteins.

Two expression vectors, pTSAPA-1 and pTSAPA-2 shown in FIG. 2, were constructed by inserting a part of the Protein A gene into an expression vector for streptavidin-containing chimeric proteins pTSA-18F as seen in FIG. 1. FIG. 1 is a schematic diagram of two expression vectors pTSA-18F and pTSA-19F for streptavidin-containing chimeric proteins. Unique cloning sites are indicted.

FIG. 2 shows expression vectors for streptavidin-Protein A chimeric proteins, pTSAPA-1 and pTSAPA-2. These vectors were constructed by inserting a part of the Protein A gene into the polylinker of pTSA-18F. The letters in the Protein A gene represent each domain of the Protein A molecule: Region S is a signal peptide; Region E, D, A, B and C are IgG binding domains; Region X is cell wall attachment domain. pTSAPA-1 encodes five IgG-binding domains with a part of the signal peptide and the cell wall attachment domain. pTSAPA-2 carries the sequence only for two IgG-binding domains, Regions E and D, with those for a part of the signal peptide and an additional IgG-binding domain, Region A. The coding sequences are flanked by the $\Phi 10$ promoter and $T\Phi$ transcriptional terminator.

pTSAPA-1 has a 960 base pairs (bp) Rsa I-BamH I fragment of pRIT11 encoding five IgG-binding domains between the Sma I and BamH I sites of pTSA-18F. pTSAPA-2 was constructed by inserting a 490 bp Rsa I-Hind III (filled-in using DNA polymerase I large fragment) fragment of pRIT11 encoding two IgG-binding domains (Regions E and D) into the Sma I and BamH I (filled-in) sites of pTSA-18F. The resulting expression vector pTSAPA-2 fragment is 3.2 kb in size. This vector encodes a chimeric protein having molecular mass of 31.4 kDa consisting of 289 amino acids residues. pTSAPA-2 encodes protein in which the Protein A moiety follows the C-terminus of streptavidin. Construction of the expression vectors was carried out by standard methods described in *Molecular Cloning, A Laboratory Manual*, Cold Spring Harbor Press (1989).

The amino acid composition of the encoded streptavidin-Protein A chimeric protein obtained from the deduced amino acid sequence, shown in Table 1, consists of 12 lysine, 3 histidine, 7 arginine, 7 aspartic acid, 14 asparazine, 33 threonine, 22 serine, 23 glutamic acid, 14 glutamine, 10 proline, 23 glycine, 33 alanine, 12 valine, 4 methionine, 9 isoleucine, 21 leucine, 9 tyrosine, 10 phenylalanine and 6 tryptophan residues. There is no cysteine residue present in the encoded streptavidin-Protein A chimeric protein. The molecular mass of the encoded protein is 31.4 kDa.

After purification, the streptavidin-Protein A chimeric protein actually expressed had almost exactly the expected molecular mass around 31 kDa.

TABLE 1

| Amino Acid Composition of Streptavidin-Protein A Chimeric Protein Encoded in pTSAPA-2 | |
|---|---|
| Amino Acid | Number |
| Lys | 12 |

TABLE 1-continued

Amino Acid Composition of Streptavidin-Protein A Chimeric Protein Encoded in pTSAPA-2

| Amino Acid | Number |
|---|---|
| His | 3 |
| Arg | 7 |
| Asp | 7 |
| Asn | 14 |
| Thr | 33 |
| Ser | 22 |
| Glu | 23 |
| Gln | 14 |
| Pro | 10 |
| Gly | 23 |
| Ala | 33 |
| Cys | — |
| Val | 12 |
| Met | 4 |
| Ile | 9 |
| Leu | 21 |
| Tyr | 9 |
| Phe | 10 |
| Trp | 6 |
| Total | 289 |
| Molecular Mass | 31.4 kDa |

Expression of Streptavidin-Protein A Chimeric Protein

Expression of gene fusions of streptavidin with Protein A is carried out essentially according to *Proc. Natl. Acad. Sci.*, 87:142 (1990).

Lysogen BL21(DE3)(pLysS) or BL21(DE3)(pLysE) transformed with an expression vector pTSAPA-1 or pTSAPA-2 is grown at 28°-42° C., preferably at 37° C., with shaking in M9 minimal medium supplemented with 1 m MMgSO$_4$, 0.2% D-glucose, 1.5 μM thiamine, 0.5% Casamino acids (Difco Laboratories), 2 μg/ml biotin, 150 μg/ml ampicillin, and 25 μg/ml chloramphenicol. While it is possible to use other suitable growth media, the minimal medium has the potential advantage that proteolysis of the expressed chimeric protein is substantially reduced. When the absorbance at 600 nm of the culture reached 1.0 for cells carrying pLysS and 0.6 for those carrying pLysE, 100 mM isopropyl β-D-thiogalactopyranoside dissolved in water is added at a final concentration of 0.5 mM to induce the T7 RNA polymerase gene placed under the lacUV5 promoter. After the induction, the cells are incubated at 28°-42° C., preferably at 37° C., with shaking for 0.5-5, preferably 1.5 to 2 hours. In general, the expressed streptavidin-Protein A chimeric protein reaches more than 20% of the total cell protein at around 2 hours after the induction. Prolonged incubation may cause degradation of the expressed streptavidin-Protein A chimeric protein.

Purification of Streptavidin-Protein A Chimeric Protein

Purification of the streptavidin-Protein A chimeric protein is performed essentially according to the method described Ibid. All procedures are carried out at 1°-10° C., preferably at 4° C. or on ice. The culture (100 ml) of BL21 (DE3) (pLysS) (pTSAPA-2) incubated for 0.1-4 hours, preferably for 2 hours, after the induction is centrifuged, preferably at 2,900×g for 5-60, preferably for 15 minutes. The cell pellet is suspended in 2-30 ml, preferably in 10 ml, of 2 mM EDTA-30 mM Tris-Cl (pH 8.0), containing 0.1% Triton X-100 and 0.5 mM phenylmethylsulfonyl fluoride to lyse the cell, and the cell lysate is stored frozen at freezing temperatures, preferably at −70° C.

To the thawed cell lysate (10 ml), 100 mM phenylmethylsulfonyl fluoride, 10 mM leupeptin, and 1.5 mM pepstatin A are added to final concentrations of 0.5 mM, 1 μM, and 1 μM, respectively. The addition of the proteinase inhibitors considerably reduces the degradation of the expressed streptavidin-Protein A chimeric protein during purification. The lysate is then treated with 10 μg/ml deoxyribonuclease I and 10 μg/ml ribonuclease A in the presence of 12 mM MgSO$_4$ at temperature 15°-30° C., preferably at room temperature, for 5-60, preferably 20 minutes. The mixture is centrifuged at 39,000×g for 5-60 preferably, 15 minutes, and the precipitate is dissolved in approximately 100 ml of 7M guanidine hydrochloride. The solution is dialyzed against 150 mM NaCl -50 mM Tris-Cl (pH 7.5) containing 0.05% Tween 20, 0.1 mM phenylmethylsulfonyl fluoride 1 μM leupeptin, 1 μM pepstatin A and 0.02% NaN$_3$. To achieve slow removal of guanidine hydrochloride, the dialysis bag containing the crude protein fraction is left for 2-24 hours, preferably overnight in the dialysis solution (approximately 1,000 ml) without stirring, followed by several changes of the dialysis solution and dialysis with stirring. The dialysate is centrifuged at 39,000×g for 5-60 minutes, preferably 15 minutes, and the supernatant is applied to an IgG Sepharose 6 fast flow column (1.2×1.1 cm, Pharmacia-LKB) previously equilibrated with 150 mM NaCl-50 mM Tris-Cl (pH 7.5), containing 0.05% Tween 20. After the application of the sample, the column is washed with 10 bed volumes of the same solution, followed by washing with two bed volumes of 50 mM ammonium acetate (pH 5.0) to remove unbound protein. The bound protein is eluted with 0.5M acetic acid adjusted pH to 3.4 with ammonium acetate. The eluted protein is dialyzed against 1.0 M NaCl-50 mM sodium carbonate (pH 11.0), and the dialysate is clarified by centrifugation at 39,000×g for 5-60 minutes, preferably 15 minutes. The supernatant is applied to a 2-iminobiotin agarose column (1.2×1.2 cm, Sigma) previously equilibrated with the same solution. The column is washed with 10 volumes of the same solution, and the bound proteins are eluted with 6M urea-50 mM ammonium acetate (pH 4.0). The eluted protein fraction is dialyzed against Tris-buffered saline (TBS), containing 150 mM NaCl-20 mM Tris-Cl(pH 7.5), and additionally containing 0.02% NaN$_3$. The dialysate is stored at 1°-10° C., preferably at 4° C. after filtration through a 0.22 μm filter (Millex GV, Millipore). For long term storage, the protein is stored frozen at temperature −20° C. or lower, preferably at −70° C.

By using two affinity chromatographies using IgG and a biotin derivative as the ligands, the expressed streptavidin-Protein A chimeric protein was purified to homogeneity.

Determination of Biotin-binding Ability

Biotin-binding ability was determined by gel filtration according to *Methods Enzymol.*, 18A:424 (1970) using a Sephadex G-25 desalting column (PD-10; 0.76×5.0 cm, Pharmacia-LKB) and D-[carbonyl-$^{14}$C]biotin (52 mCi/mmol, Amersham). The binding of the chimeric protein to biotin was done at room temperature in TBS containing 0.02% NAN$_3$, and the same solution was used as the eluent.

Determination of IgG-binding Ability

The purified chimeric protein (approximately 50 μg, 1.6 nmol subunits) was immobilized on a 2-iminobiotin agarose column (0.8×0.4 cm, 200 µl, Sigma) equilibrated with 1.0M NaCl/50 mM sodium carbonate, pH 11.0/0.02% NAN$_3$, and the column was then equilibrated with 2 ml of TBS containing 0.02% Tween 20 and 0.02% NaN$_3$. Excess amounts of human IgG (1.2 mg, 8 nmol, Sigma) dissolved in the same solution were applied to the column, and allowed to bind to the immobilized chimeric protein. The column was washed with 2 ml of the same solution to remove unbound IgG, and the chimeric protein-IgG complex was eluted with 6M urea/50 mM ammonium acetate, pH 3.5. Protein concentration of the eluate was determined by measuring the absorbance at 280 nm using $\underline{E}^{0.1\%}{}_{280\ nm}$ 1.6 for the chimeric protein and $\underline{E}^{0.1\%}{}_{280\ nM}$ 1.4 for IgG. The amount of the chimeric protein was also estimated by a biotin-binding assay. Comparison of the eluate to the control, which was without the application of IgG, gave the amount of bound IgG.

Immunoblotting Analysis

Immunoblotting analysis was carried out as previously described in *Proc. Natl. Acad. Sci.*, 87:142 (1990) with some modifications. The primary and the secondary antibodies used were rabbit anti-serum to streptavidin (Sigma) and donkey anti-rabbit Ig F(ab')$_2$ fragment conjugated to horseradish peroxidase (Amersham), respectively. The peroxidase activity was detected by the ECL system (Amersham) which is based on the oxidation of luminol.

Targeting Biotinylated Molecules to Antigen-Antibody Complexes

Molecular mass standard proteins consisting of six proteins (phosphorylase b, 94 kDa; BSA, 67 kDa; ovalbumin, 43 kDa; carbonic anhydrase; 30 kDa; trypsin inhibitor, 20.1 kDa; α-lactalbumin, 14.4 kDa, Pharmacia-LKB) were separated by SDS-PAGE (12.5% acrylamide), and the electroblotted onto a nitrocellulose membrane (4.3×7.0 cm, pore size 0.45 µm) obtained from Schleicher & Schuell by a discontinuous buffer systems described in *J. Biochem. Biophys. Methods*, 10:203 (1984) using NovaBlot (Pharmacia-LKB). The membrane was incubated at room temperature for 1 hour in 3% gelatin dissolved in TBS to block reactable sites of the membrane. The membrane was then incubated with mouse monoclonal anti-bovine serum albumin (BSA) IgG$_2$ in TBS containing 1% gelatin and 0.02% Tween 20, and the antibodies were allowed to bind for 1 hour. Unbound antibodies were removed by washing the membrane with TBS containing 0.02% Tween 20. The purified streptavidin-Protein A chimeric protein (30 µg, 0.96 nmol subunits) was conjugated to biotinylated horseradish peroxidase at a molar ratio of peroxidase to chimeric protein subunit of 1. The membrane was incubated with the chimeric protein-peroxidase conjugates in TBS containing 1% gelatin and 0.02% Tween 20 for 1 hour to allow the conjugates to bind to the antigen (BSA)-antibody (anti-BSA) complex. Unbound conjugates were removed by washing, and the peroxidase activity on the membrane was detected by the ECL system.

Gel Filtration Chromatography

Gel filtration chromatography was carried out at room temperature using a Sephadex G-200 column (1.6×80 cm, Pharmacia-LKB). The purified streptavidin-Protein A chimeric protein (100 µg, 3.2 nmol subunits) was saturated with biotin by adding excess amounts of D-[carbonyl-$^{14}$C]biotin (4.8 nmol), and applied to the column previously equilibrated with TBS containing 0.05% Tween 20 and 0.02% NaN$_3$. The proteins were eluted with the same solution at a flow rate of 7.7 ml per hour, and fractionated. The radioactivity of each fraction was determined by liquid scintillation counting (Tri-Carb 2000CA, Packard) using Ready Safe scintillation fluid (Beckman). Molecular mass of the chimeric protein was estimated by calibration with molecular mass standard proteins obtained from Pharmacia-LKB. The natural Protein A was also used for estimation.

SDS-PAGE Analysis

SDS-PAGE was performed with a discontinuous buffer system according to *Nature*, 227:680 (1970) using a 12.5% acrylamide gel. Proteins were stained with Coomassie Brilliant Blue R-250 dissolved in 45% methanol/10% acetic acid.

DETAILED DESCRIPTION OF FIGURES

Expression of Streptavidin-Protein A Chimetic Protein

To express gene fusions of streptavidin with Protein A, the T7 expression system was used with which it was possible to successfully express a cloned streptavidin gene in *E. coli*. With the expression vector pTSAPA-1 encoding five IgG-binding domains, no appreciable expression of the 48 kDa protein was observed on SDS-PAGE of the total cell protein. By immunoblotting analysis using anti-streptavidin, multiple protein bands were observed ranging from 20–45 kDa. These results suggested that the chimeric protein encoded in pTSAPA-1 was expressed, but that it was susceptible to proteolysis in the host cells. In addition, the size of the protein bands on the immunoblots indicated that the hinge regions between the IgG-binding domains were particularly labile, and that those close to the C-terminus were more susceptible to proteolysis.

Figure 3:
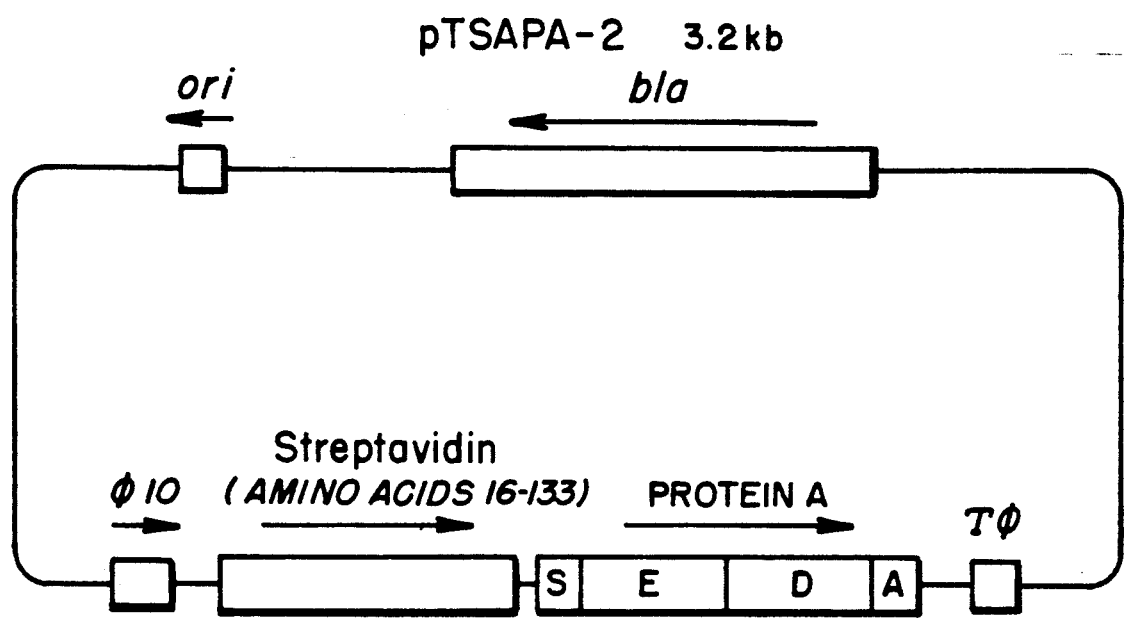
FIG. 3 represents expression vector pTSAPA-2 for streptavidin-Protein A chimeric protein.

To minimize the proteolysis of the expressed chimeric protein in the cells, the C-terminal region of the Protein A moiety was truncated and the expression vector pTSAPA-2 which encodes only two IgG-binding domains (FIGS. 2 and 3) was constructed and used.

Figure 5:
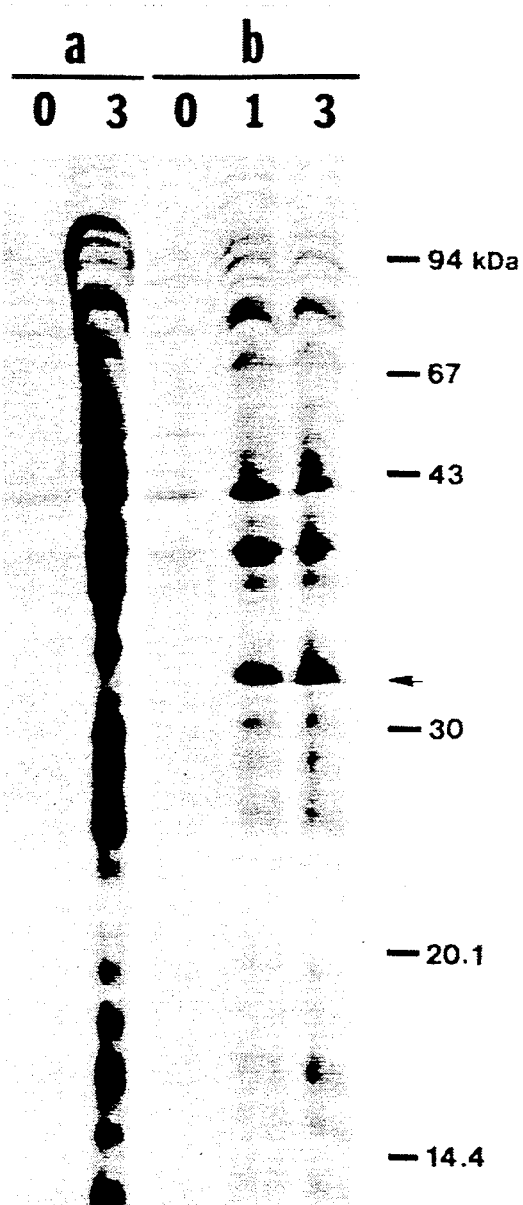
FIG. 5 is SDS-PAGE of total cell protein, stained with Coomassie Brilliant Blue, during expression using BL21(DE3)(pLysS) with or without the expression vector pTSAPA-2.
Figure 6:
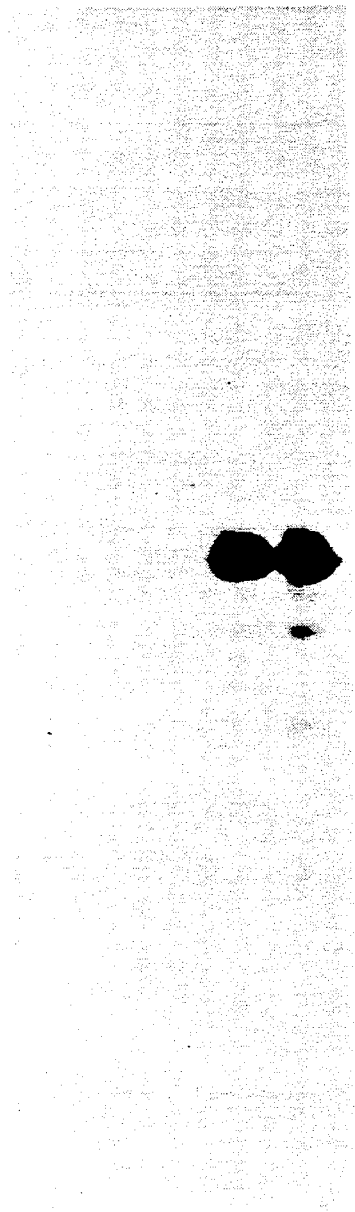
FIG. 6 are immunoblots of SDS-PAGE using antiserum to streptavidin, of total cell protein of BL21(DE3)(pLysS) with or without pTSAPA-2.

FIGS. 5 and 6 show the expression of streptavidin-Protein A chimeric protein using pTSAPA-2. Total cell protein of BL21(DE3)(pLysS) with or without pTSAPA-2 was subjected to SDS-PAGE (12.5% acrylamide), protein stained with Coomassie Brilliant Blue R-250 (FIG. 5); FIG. 6 are immunoblots using antiserum to streptavidin. Lanes a, BL21(DE3)(pLysS); b, BL21 (DE3)(pLysS)(pTSAPA-2). The number above each lane is the time after the induction in hours. The 31 kDa protein is indicated by arrows. Positions of molecular mass standard proteins (94, 67, 43, 30, 20.1, and 14.4 kDa) for FIG. 5 and prestained standard proteins (80, 45, 33, 26, and 19.5 kDa) for FIG. 6 are indicated. For (FIG. 5), each lane contains the total cell protein rom 167 µl culture except for lane a at 3 hours, where 83 µl of culture was used. For (FIG. 6), the total cell protein from 42 µl of culture was applied in each lane.

SDS-PAGE analysis of the total cell protein seen in FIG. 5, shows that a 31 kDa protein, which is consistent with the molecular mass estimated from the deduced amino acid sequence, as seen in Table 1, was efficiently expressed in the host cells after the induction. In addition, the 31 kDa protein cross-reacted with anti-streptavidin (FIG. 6) suggesting that this protein is the streptavidin-Protein A chimeric protein. Immunoblotting analysis also shows that almost no degradation of the expressed chimeric protein occurred, indicating that the truncation of the C-terminal IgG-binding domains considerably reduced intracellular proteolysis of the expressed chimeric protein. The expressed chimeric protein generally reached more than 20% of the total cell protein at 2 to 3 hours after the induction in BL21(DE3)(pLysS)(pTSAPA-2). Extended incubation caused degradation of the expressed chimeric protein in the cells. BL21(DE3)(pLysE)(pTSAPA-2) had a lower expression efficiency than the equivalent carrying pLysS, in contrast with the cases for the expression vectors pTSA-2 described in *Proc. Natl. Acad. Sci.*, 87:142 (1990) and pTSA-21 in BBRC, 176:571 (1991) for recombinant streptavidin molecules. In addition, more degradation of the expressed chimeric protein was observed in BL21(DE3) (pLysE)(pTSAPA-2).

Characterization of Purified Streptavidin-Protein A Chimeric Protein

The expressed chimeric protein formed inclusion bodies in the host cells, as generally observed in *E. coli* over-expression systems. After the inclusion body fraction was dissolved in guanidine hydrochloride, followed by slow removal of guanidine hydrochloride, the expressed chimeric protein renatured, and could be specifically purified to homogeneity as seen in FIG. 4 by two affinity chromatographic methods each using human IgG or a biotin derivative as the ligand.

Figure 4:
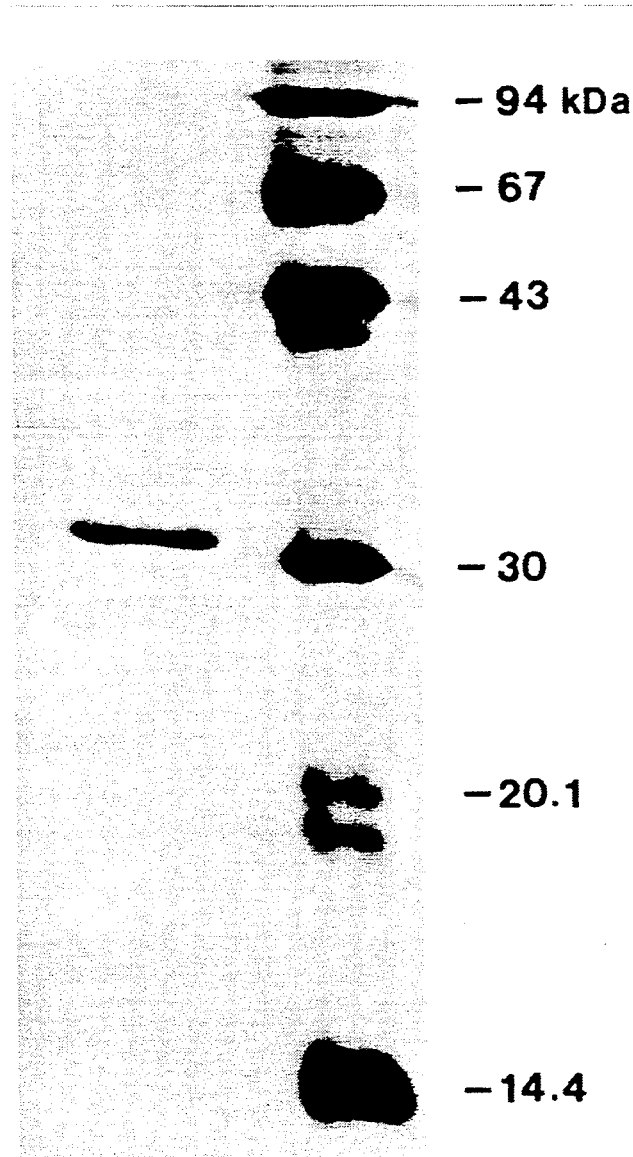
FIG. 4 is SDS-PAGE analysis of purified streptavidin-Protein A chimeric protein.

FIG. 4 shows SDS-PAGE analysis of purified streptavidin-Protein A chimeric protein. Approximately 2.5 μg of the purified streptavidin-Protein A chimeric protein was subjected to SDS-PAGE (12.5% acrylamide). Proteins were stained with Coomassie Brilliant Blue R-250. The right lane contains molecular mass standard proteins.

The purified chimeric protein bound more than 0.96 molecules of biotin per subunit (31.4 kDa), indicating that the chimeric protein had full biotin-binding ability. In addition, the chimeric protein bound one IgG molecule per subunit. Both the native Protein A, containing five IgG-binding domains, and a recombinant Protein A, containing two IgG-binding domains (Ljungquist, 1989), bind two IgG molecules. The lower IgG-binding ability of the chimeric protein was probably caused by stearic hindrance resulting from the streptavidin moiety or from subunit association. However, the IgG-binding ability was independent of the biotin binding.

Figure 7:
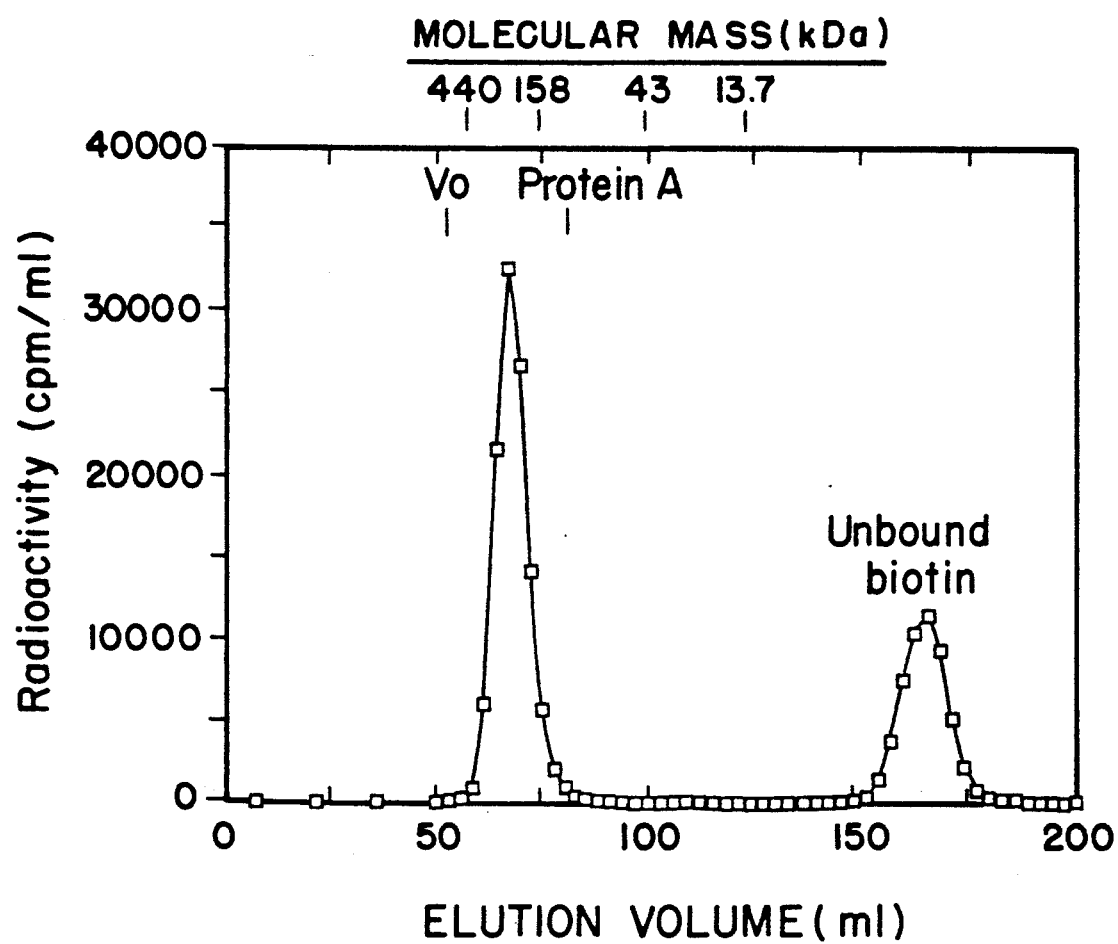
FIG. 7 is gel filtration chromatography of purified streptavidin-Protein A chimeric protein.

Gel filtration chromatography of purified streptavidin-Protein A chimeric protein is shown in FIG. 7. The purified streptavidin-Protein A chimeric protein (100 μg, 3.2 nmol subunits) was saturated with biotin by adding 4.8 nmol of D-[carbonyl-$^{14}$C]biotin, and applied to a Sephadex G-200 column (1.6×80 cm) previously equilibrated with 150mM NaCl/20 mM Tris-Cl, pH 7.5/0.05% Tween 20/0.02% NaN$_3$. Proteins were eluted at room temperature with the same solution at a flow rate of 7.7 ml per hour, and collected in 2.83 ml fractions. The radioactivity of each fraction was determined by liquid scintillation counting. The positions where molecular mass standard proteins were eluted are shown at the top: Ferritin, 440 kDa; aldolase, 158 kDa; ovalbumin, 43 kDa; RNase A, 13.7 kDa. The position where the natural Protein A (42 kDa) was eluted is also indicated.

By gel filtration chromatography as seen in FIG. 7, the purified chimeric protein showed a single sharp peak, and its molecular mass was estimated to be 180–190 kDa by calibration with molecular mass standard proteins. However, Protein A is known to have a markedly extended shape (Björk et al., 1972; Sorolia et al., 1982; Lindmark et al., 1983). Thus, it is likely that the chimeric protein would elute faster than expected on gel filtration chromatography because of the extended structure of its Protein A moiety. The molecular mass of the natural Protein A molecule (42 kDa) was estimated to be approximately 100 kDa by gel filtration chromatography using the same column. Similar results were also obtained, when other gel filtration media such as Sephacyl S-300HR were used. Taking into account the chromatographic behavior of the Protein A molecule on gel filtration, we conclude that the chimeric protein forms a subunit tetramer. Because the natural streptavidin molecule forms a subunit tetramer (Green, 1975, 1990), it is quite reasonable to conclude that the subunit association of the chimeric protein is determined by its streptavidin moiety. Therefore, one streptavidin-Protein A chimeric protein consisting of four subunits should bind four biotin and four IgG molecules.

Conjugation or Labelling Biological Materials with Antibody Molecules Using Streptavidin-Protein A Chimeric Protein Protein A possesses the capacity for binding to immunoglobulins, particularly to IgG. Such binding occurs through an interaction of the Protein A and the Fc portion of gamma globulins but it does not involve reactivity with Fab areas involved in the antibody combining regions with antigens. This feature is important for second type of biological recognition ability of the current invention. While the Fab region of the antibody allows the binding of antibody to the antigen and the Fc domain binds to the chimeric protein of the current invention, the site of the antigen can be easily located and a quantity of the antigen can be determined.

Conjugation of antibody molecules with the streptavidin-Protein A chimeric protein can be done by simply mixing antibodies and the chimeric protein. Because of the species and subclass specific binding affinity of Protein A for antibodies, one can selectively conjugate or label specific antibody molecules from the mixture. Because of the pH dependent binding of Protein A with antibodies, low pH conditions are preferably avoided. The antibody and the streptavidin-Protein A chimeric protein complex or antigen antibody-streptavidin-Protein A chimeric protein can be directed to any biological materials containing biotin. Because of the extremely low dissociation constant of the streptavidin-biotin complex, excess amounts of the complex of the antibody and the streptavidin-protein chimeric protein are unnecessary. The order of the conjugation can be varied without altering the final results.

Targeting Biotinylated Molecules to Antigen-antibody Complexes

Figure 8:
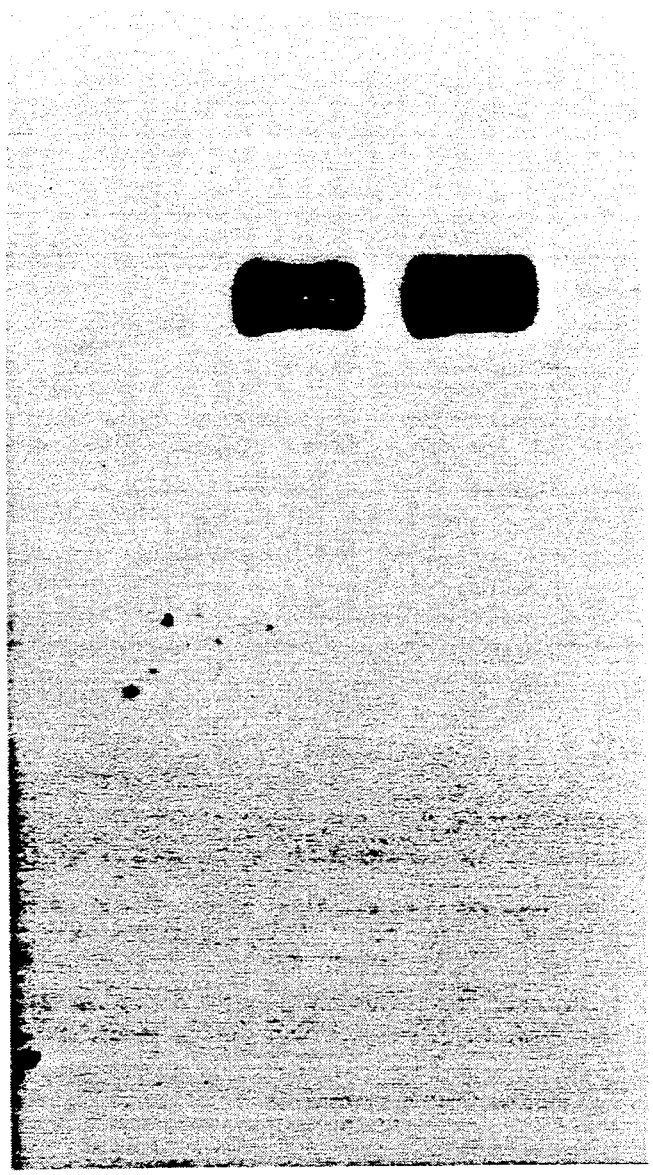
FIG. 8 illustrates specific detection of bovine serum albumin.
Figure 9:
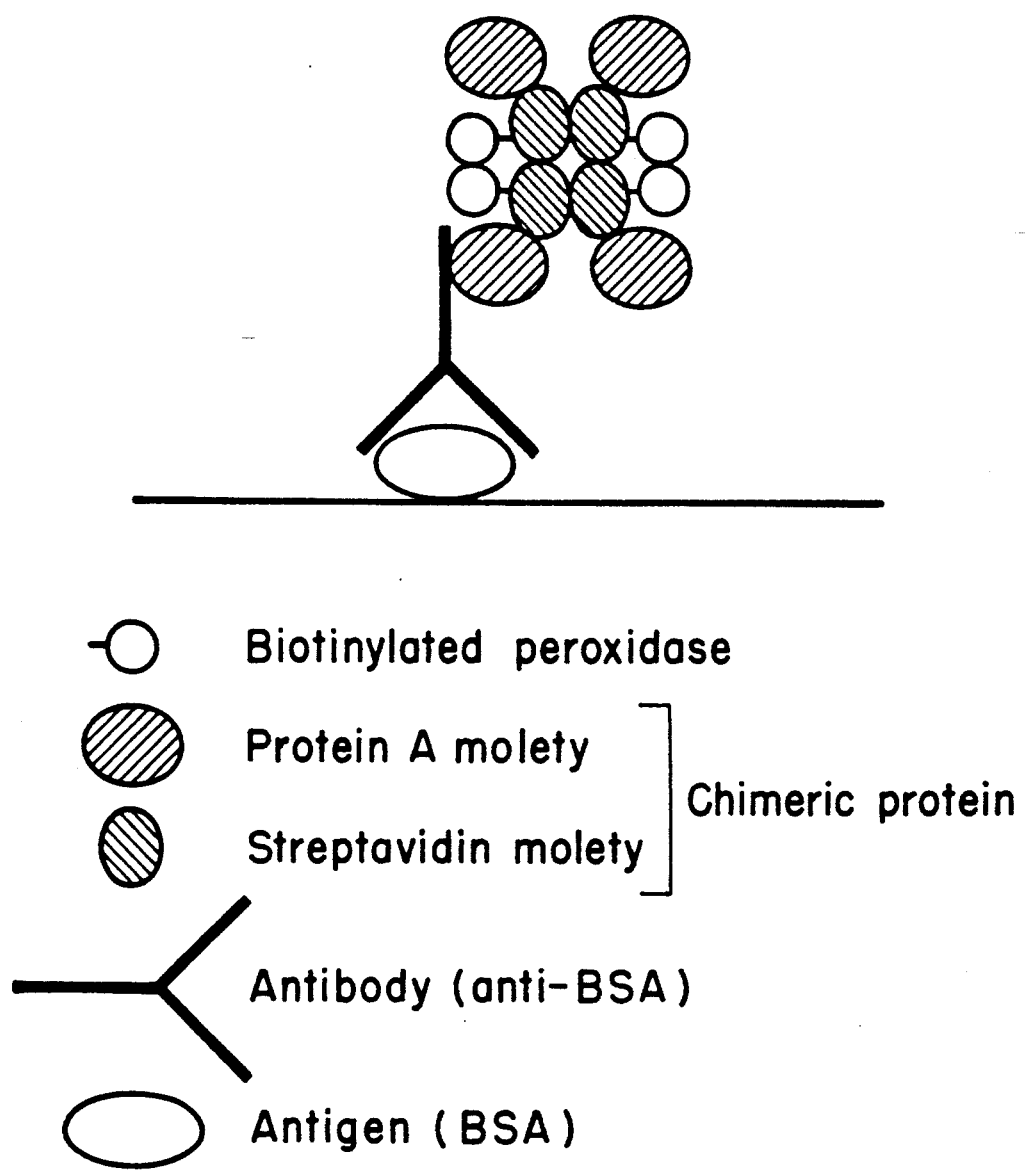
FIG. 9 is a schematic diagram of an antigen molecule bovine serum albumin, bridged to peroxidase through an antibody, anti-bovine serum albumin, and streptavidin-Protein A chimeric protein.

To demonstrate the capability of the streptavidin-Protein A chimeric protein to specifically conjugate antibody molecules to other biological molecules, a biotinylated molecule was targeted to an antigen-antibody complex using the chimeric protein. Molecular mass standard proteins consisting of six proteins were separated by SDS-PAGE, and biotinylated peroxidase was targeted to one of the components, BSA, using a monoclonal antibody to BSA (anti-BSA) and the chimeric protein. By using this system detected by peroxidase activity, BSA was specifically labelled with peroxidase and results are shown in FIG. 8, indicating that the antigen molecule (BSA) was specifically bridged to the biotinylated peroxidase molecule through the antibody (anti-BSA) and the chimeric protein as seen in FIG. 9. The high binding specificity of the Protein A moiety to an IgG molecule is demonstrated by the fact that no background signal, produced by non-specific binding to other components or the blocker (gelatin) was observable. Since extensive washing steps were included in this system, the result also reveals that the chimeric protein retains the tight binding affinity both for a biotinylated molecule and an antibody molecule, that the natural streptavidin and Protein A molecules possess.

FIG. 8 illustrates specific detection of BSA using streptavidin-Protein A chimeric protein and mouse monoclonal antibody to BSA. Molecular mass standard proteins (phosphorylase b, 94 kDa; BSA, 67 kDa; ovalbumin, 43 kDa; carbonic anhydrase, 30 kDa; trypsin inhibitor, 20.1 kDa; α-lactalbumin, 14.4 kDa) were separated by SDS-PAGE (12.5% acrylamide), and electroblotted onto a nitrocellulose membrane. After reactable sites of the membrane were blocked with gelatin in TBS, mouse monoclonal anti-BSA (IgG$_2$) was allowed to bind for 1 hour. After bound antibodies were removed, the membrane was incubated with purified streptavidin-Protein A chimeric protein conjugated to biotinylated horseradish peroxidase for 1 hour. Unbond chimeric protein-peroxidase complexes were removed, and the peroxidase activity on the membrane was detected by the ECL system. The positions of the molecular mass standard proteins are indicated. Lanes a, b, and c contain 5, 50, and 250 ng BSA, respectively.

FIG. 9 is a schematic diagram of an antigen molecule (BSA) bridged to peroxidase through an antibody (anti-BSA) and streptavidin-Protein A chimeric protein.

The streptavidin-Protein A chimeric protein is thus capable of providing antibody molecules with additional biological recognition capability, in addition to their natural antigen recognition. This characteristic of the streptavidin-Protein A chimeric protein extensively expands the application of antibodies by the use of specific conjugation or targeting of antibody molecules to other biological materials containing biotin. The potential ability of biotin to be easily incorporated into various biological materials, including proteins, nucleic acids, carbohydrates, lipids, cells, and tissues facilitates the application of the chimeric protein to a broad range of biological materials.

UTILITY

Antibodies are one of the most useful biological tools because of their specificity and variation. To take advantage of their multiple utility and to make antibody molecules capable of specific conjugation or labelling with other biological materials, a streptavidin-Protein A chimeric protein of this invention was designed.

Since streptavidin specifically binds a water soluble vitamin D-biotin in remarkably high affinity ($K_d \sim 4 \times 10^{-14}$M) and since biotin can be easily incorporated into various biological substances, the novel streptavidin-Protein A chimeric protein which also binds antibodies through its Protein A region offers a variety of applications such as detection, isolation, and characterization of biological substances as well as therapeutic and diagnostic use of the materials which bind to such chimeric protein. With the specific and tight binding of the streptavidin-Protein A chimeric protein both with IgG molecules and with biotin, any biological material containing biotin can be easily conjugated or labelled with antibodies. Such antibodies then may be introduced to such biological materials for therapeutic purposes, for diagnostic purposes or for identification purposes. Other potential uses of the chimeric proteins of this invention are for detection of antibodies, immobilization of antibody, increasing antibody-antibody affinity, DNA tagging or multilabelling of biological materials.

Novel features of the current invention include the two-sided biological recognition specificity of the streptavidin-Protein A chimeric portein or its conjugate to an antibody. One-side specificity is caused by high affinity binding of the Protein A side of the streptavidin-Protein A chimeric Protein A chimeric protein to antibody molecules or that of an antibody bound to the Protein A side of the chimeric protein. Second-side specificity is caused by high affinity binding of the streptavidin side of streptavidin-Protein A to any target biological material which contains biotin or which is capable of being biotinylated.

Another novel feature of this invention is that various antibody molecules or antigen-antibody complexes can be introduced into biological materials containing biotin without any complex procedures or treatments, in limited amounts to those bound to a chimeric protein.

The multiple conjugation or labelling of the target molecules can be done by repeating the binding cycle of the antibody-streptavidin-Protein A chimeric protein complex labelled with dyes, enzymes, marker proteins, or radioactive markers, to the target.

Since most biological materials, such as proteins, nucleic acids, carbohydrates, lipids, cells, tissues, can be biotinylated, any biological materials can be easily conjugated or labelled with antibodies according to this method. In addition, antibody molecules are delivered into and specifically directed to such biological materials containing biotin.

In addition, DNA-antibody complexes can be easily constructed after the biotinylation of the DNA molecules. These DNA-antibody complexes allow the specific and sensitive detection of the target molecules bound to the antibody by amplifying the attached DNA molecule by polymerase chain reaction. Alternatively, the target molecules can be detected by observing RNA or protein molecules after transcription or transcription-translation, respectively, of the attached DNA molecules. Since Protein A binds to antibodies dependent on their host species and subclasses, the invention is useful to selectively direct biological materials containing biotin to other biological materials bound to specific antibodies.

Because of the tight binding characteristic of streptavidin with biotin, Protein A, Protein A-antibody, or Protein antigen complexes can be immobilized on solid supports, allowing easy separation and purification of target molecules, such as antigens, antibodies, and antigen-antibody complexes.

The cycles of the binding of antibody molecule with the target and the binding of the streptavidin-Protein A chimeric protein conjugated with some maker protein or dye to the antibodies can be easily repeated. This generates multiple labelling of the target molecules with different markers. Radioactive biotin and its derivatives can be easily incorporated into the chimeric protein, and thus it allows introduction or labeling of biological materials with radioisotopes through antibodies against such targets.

Streptavidin-Protein A-conjugated antibody is generally useful for preventive, therapeutic and diagnostic purposes.

The usefulness of the current invention in prevention and treatment of these infection would be in both healthy or acutely and chronically ill patients whose immune defenses are considerably weakened or non-existent due to the long illness or suppression of the immune system. AIDS patients, or transplant recipients would be primary subjects for such treatment with streptavidin-Protein A-antibody complexes. Since the Fc domain of the antibody is tightly bound to the Protein A moiety of the chimeric protein, Fab region is exposed and available to bind selectively specific or nonspecific antigens. However, it must be understood that to prevent immunological reactions against bacterial proteins, and that such treatment could in most cases be administered only once.

For diagnostic purposes, the current invention is useful in recognizing a presence of immune complexes in various tissues or tissue lesions, circulating immune complexes. In this instance, sole streptavidin-Protein A chimeric protein, non-complexed with an antibody, would be administered to a patient. Such protein would be preferably labeled with radioisotopes such as $^{125}I$. When encountering the antigen-antibody complex, it would bind to the antibody the Fc domain of, thus resulting in streptavidin Protein A-antibody-antigen complex containing radioisotopes which could be detected by various detection and analytical methods available in the art. This detection method would be generally useful for detection of all antibody-antigen complexes, which would then be isolated and the antigen-antibody identified by known methods.

In many diseases, such as in rheumatoidal arthritis, systemic lupus erythematosus, dermatomyositis, scleroderma, periarteritis or even acute rheumatic fever, the chronic inflammation of tissue is caused by the presence of antigen-antibody complexes in these tissues. Since until now specific antigens for these diseases was not identified (*Immune Complexes in Clinical and Experimental Medicine*, p. 197, R. C. Williams, Harvard University Press (1980)), the current chimeric protein would be useful for both diagnostic purposes to show and identify the presence of these antigen-antibody complexes, but also for therapeutic purposes where the lavage or perfusion with these chimeric proteins would be able to remove these complexes from the tissue and in this way prevent further inflammations and spread of the disease.

Similarly, tumor antigens could be both identified and disactivated by binding to chimeric proteins of this invention either as antigen alone bound to streptavidin-Protein A-antibody or antigen-antibody bound to streptavidin-Protein A chimeric protein. The later is particularly excellent candidate for prevention and treatment of neoplastic growth because it is well known that in many instances the natural bodily immune systems provide the enhancement or facilitation of tumor growth (Ibid., p.255).

The current invention would also be useful in prevention and amelioration of hypersensitivity reactions associated with allergens. In this case, the chimeric protein-antibody complexes would be administered which would deactivate the allergen by binding it to the antibody. These proteins would be, for example, administered to a patient in anaphylactic shock without or together with histamines.

These and other uses of the streptavidin-Protein A chimeric protein in all immunological reaction and for treatment and prevention of immune diseases or complications are intended to be within the scope of this invention. The examples below are enclosed only for illustrative purposes and should not be considered to limit the current invention in any way.

MATERIALS AND METHODS

Materials

Restriction endonucleases, T4 DNA ligase, and DNA polymerase I large fragment were obtained from New England Biolabs or Boehringer Mannheim. 2-Iminobiotin agarose, anti-serum to streptavidin, human IgG, mouse monoclonal antibody to bovine serum albumin (BSA), phenylmethylsulfonyl fluoride, and guanidine hydrochloride (Grade I) were from Sigma. Donkey anti-rabbit Ig F(ab')$_2$ conjugated to horseradish peroxidase, the enhanced chemiluminescence (ECL) detection system, and D-[carbonyl-$^{14}$C]biotin were from Amersham. Molecular mass standard proteins for SDS-PAGE and gel filtration chromatography, IgG Sepharose 6 Fast Flow, Sephadex G-200, and Sephadex G-25 columns (PD-10) were from Pharmacia-LKB. Prestained molecular mass standard proteins for SDS-PAGE, Tween 20 (Enzyme Immunoassay grade), and gelatin (Enzyme Immunoassay grade) were from BioRad. Natural Protein A, biotinylated horseradish peroxidase, leupeptin, and pepstatin A were for Boehringer Mannheim. Other reagents were analytical grade.

Bacterial Strains and Plasmids

*E. coli* strains HMS174 *Proc. Natl. Acad. Sci.*, 75:2276 (1978) and DH5α (Sambrook et al., *Molecular Cloning: A Laboratory Manual*, 2nd Ed., Cold Spring Harbor Laboratory Press 1989) were used for cloning. Lysogen BL21(DE3) *J. Mol. Biol.*, 189:113, *Methods Enzymol.*, 185:60 (1990) was used for expression. This lysogen carries the cloned T7 RNA polymerase gene in the chromosome under the lacUV5 promoter.

pTSA-18F is an expression vector for streptavidin-containing chimeric proteins *Biochem. Biophys. Res. Commun.*, 176:571 (1991). This plasmid carries the DNA sequence for amino acid residues 16–133 of mature streptavidin, followed by a polylinker region, under the T7 promoter Φ10 *Methods Enzymol.*, 185:60 (1990). pRIT11 obtained from M. Uhlén, Royal Institute of Technology, Sweden, *EMBO J.*, 5:2393 (1986) carries the Protein A gene corresponding to the signal peptide (Region S) and the five IgG-binding domains (Regions E, D, A, B, and C), followed by a polylinker placed in the sequence for the cell wall attachment domain (Region X). pLysS and pLysE carrying the cloned T7 lysozyme gene were used to reduce the basal level of T7 kNA polymerase activity in the host cells.

EXAMPLE 1

Labeling of Biological Materials with Antibodies and Vice Versa

This example describes a method to specifically label a protein, horseradish peroxidase, with a monoclonal antibody to BSA using the streptavidin-Protein A chimeric protein of this invention. A similar method was employed to specifically detect the BSA molecules immobilized on a nitrocellulose membrane, as described above.

The purified streptavidin-Protein A chimeric protein (50 µg, 1.6 nmol subunits) dissolved in TBS (1.50 mM NaCl/20 mM Tris-Cl, pH 7.5) was mixed with 0.24 mg (1.6 nmol) of mouse monoclonal antibody to BSA (IgG$_2$, Sigma) in TBS. The antibody was bound to the Protein A moiety of the chimeric protein without disturbing their antigen recognition capability. The resulting antibody-chimeric protein conjugates have four antibody molecules per chimeric protein. The conjugates were then mixed with 16 µg (0.4 nmol) of biotinylated horseradish peroxidase (Sigma) in TBS. Because of the high affinity of the streptavidin moiety for biotin, the biotinylated peroxidase was bound to the chimeric protein. The resulting antibody-chimeric protein-peroxidase contains four antibody and one peroxidase molecules per chimeric protein. Thus the peroxidase was labeled with the monoclonal antibodies through the chimeric protein. The antibodies in the conjugates have the ability to bind the antigen, i.e., BSA. Thus this conjugate can be used, for example, to detect BSA by peroxidase reaction in immunoblotting analysis.

Similar procedures can be used to label other biological materials with antibodies. Because many biotinylation methods have been developed (Methods Enzymol. Vol. 184), a variety of biological materials, including proteins, nucleic acids, carbohydrates, lipids, and cells, can be labeled with antibodies, after biotinylation of a target biological material followed by conjugation to the streptavidin-Protein A chimeric protein containing antibodies. Because of the high affinity of the chimeric protein both for IgG and biotin, conjugation can be done simply by mixing the chimeric protein, biotinylated molecules, and antibodies at an appropriate ratio, and no complex procedure is required.

EXAMPLE 2

Construction of DNA-antibody Complexes After the Biotinylation of the DNA Molecule This example describes a method to construct a linearized plasmid DNA-antibody complex using the streptavidin-Protein A chimeric protein of this invention. The techniques used to manipulate DNA are the standard ones, as described in *Molecular Cloning: Laboratory Manuals*, (Cold Spring Harbor Press, 1989), unless otherwise stated.

Plasmid pUC19 was digested with Hind III and Acc I to completion. The termini of the linearized plasmid were filled-in using the large (Klenow) fragment of *E coli* DNA polymerase I in the presence of dCTP, dTTP, dGTP, and biotinylated dATP (biotin-16-dATP, BRL). Because biotinylated dATP is incorporated only into the terminus generated by Hind III site, the resulting blunt-ended DNA molecule contains one biotin molecule at the end. Unincorporated nucleotides and a 21 bp Hind III-Acc I fragment were removed by repeated filtration through Centricon 30 (Amicon), and a 2.67 kb fragment was purified.

To construct the antibody-chimeric protein conjugates, the purified streptavidin-Protein A chimeric protein (1.0 µg, 8 pmol molecules, 32 pmon subunits) dissolved in TBS (150 mM NaCl/20 mM Tris-HCl, pH 7.5) was mixed with 1.2 µg (8 pmol) mouse monoclonal antibody to BSA (IgG$_2$, Sigma) dissolved in the same solution. The resulting antibody-chimeric protein conjugate, in which the antibody was bound to the Protein A moiety of the chimeric protein, has one antibody molecule per chimeric protein. To the antibody-chimeric protein conjugates, 15 µg of the biotinylated 2.67 kb linear pUC19 DNA containing 8 pmol biotin was added. The biotin molecule incorporated into the terminus of the DNA molecule was bound to the streptavidin moiety of the chimeric protein. The resulting conjugates have one antibody molecule and one 2.67 kb linear DNA per chimeric protein. Thus, the antibodies and the linear pUC19 DNA molecules were conjugated at 1:1 ratio through the streptavidin-Protein A chimeric protein. This conjugate had the ability to bind the antigen, i.e., BSA, and thus could be used to target the DNA molecule to the antigen (BSA), which is, for example, immobilized on a membrane or microtiter plate. When the antigen-antibody complexes are formed, the bound DNA molecules can be detected by various methods which are currently used in molecular biology. Such methods include amplification of a specific region by PCR (polymerase chain reaction), hybridization with specific probes, and incorporation of specific dyes to the DNA. When an appropriate promoter is contained in the DNA molecule of such conjugates, transcription or transcription-translation assay can be used.

In this example, the conjugation of the antibody to the chimeric protein was first done. However, one can first conjugate DNA to the chimeric protein, and then conjugate to antibodies. The order of the conjugation does not affect the properties of the final DNA-antibody complexes. There are many ways to biotinylate DNA molecules, e.g., random biotinylation using a biotin derivative containing a photo-activatable group, extension reaction using a DNA polymerase in the presence of biotinylated nucleotides, and PCR with biotinylated primers. The appropriate ratio of the chimeric protein to the target DNA should be determined to facilitate effective conjugation.

EXAMPLE 3

Selective Transfer of Biotin and Biotin-containing Materials to Biological Materials Containing or Bound to Specific Antibody This example describes a method of labeling cells with FITC by targeting biotinylated FITC to antibodies bound to antigens on the surface of a cell using the streptavidin-protein A chimeric protein of this invention.

Mouse T-cells are prepared by standard techniques, and suspended in Dulbecco's PBS containing 1% fetal bovine serum and 0.1% NaN$_3$. Anti-(Thy-1 antigen) is added to the cell suspension, and the mixture is incubated on ice for 30 minutes. The antibody binds to the Thy-1 antigen on the surface of the cell. Unbound antibodies are removed by washing the cell with the same solution. The purified streptavidin-Protein A chimeric protein (50 µg, 0.4 nmol molecules, 1.6 nmol subunits) in the same solution is mixed with 1.6 nmol biotinylated FITC (Boehringer Mannheim). The biotin-binding sites of the chimeric protein are saturated with FITC. The FITC-chimeric protein conjugates are added to the cell suspension, in which the anti-(Thy-1 antigen) is bound to the surface of the cell. The Protein A moiety of the chimeric protein binds to the antibody on the cell surface, and thus the FITC molecules are specifically targeted to the antibodies bound to the cell surface antigens. Unbound FITC-chimeric protein conjugate are removed by washing the cells with the same solution.

By this procedure, biotinylated FITC is specifically introduced onto the T cells which have the antibodies on their surface. Thus, the T cells are specifically labeled with FITC. Such FITC-labeled cells can be detected and analyzed by FACS (fluorescence activated cell sorter) or fluorescence microscopy. Using a similar procedure, various marker molecules containing biotin can be specifically targeted to the surface of the cells. This technique allows transfer or target biotinylated molecules to other biological materials containing antibodies.

EXAMPLE 4

Immobilization of Protein A or Protein A-Antibody-Complex to Purify Antibodies or Antigens This example describes a method to immobilize Protein A on an agarose matrix using the streptavidin-Protein A chimeric protein of this invention, and its use to isolate human IgG from crude solution. A similar technique was employed to determine the IgG-binding ability of the steptavidin-Protein A chimeric protein A, as described above.

The purified streptavidin-Protein A chimeric protein (50 µg, 0.4 nmol molecules, 1.6 nmol subunits) is dialyzed against TBS (150 mM NaCl/20 mM Tris-Cl, pH 7.5), and the dialysate is clarified by centrifugation at 39,000×g for 15 minutes. The supernatant is applied to a column containing biotin-agarose (200 µl; Sigma) previously equilibrated with TBS. The streptavidin moiety of the chimeric protein efficiently binds to biotin, and thus the chimeric protein is immobilized stably on biotin-agarose. Unbound proteins are removed by washing the column with the same solution. Because of the tight binding affinity of the streptavidin for biotin, the bound chimeric proteins would not be released from the column by repeated washing.

Crude human IgG solution prepared from human serum is dialyzed against 10 mM sodium phosphate, pH 7.4, and the dialysate is clarified by centrifugation at 39,000×g for 20 minutes. The column with the immobilized chimeric protein is equilibrated with 10 mM sodium phosphate, pH 7.4, and the supernatant is applied to the column. IgG molecules are bound to the Protein A moiety of the chimeric protein, and other components, such as albumins, $\alpha$- and $\beta$-globulins, are removed by washing the column with the same solution. The bound IgG can be eluted with 0.1M glycine-HCl, pH 2.8. The eluted fraction contains $IgG_1$, $IgG_2$, and $IgG_4$. Similar techniques can be used to isolate IgG molecules of other species, such as rat, mouse, and goat. In addition, by changing the binding and elution conditions, one can isolate specific subclass of IgG. Under the following conditions, for example, mouse $IgG_1$ can be specifically isolated from $IgG_{2a}$ and $IgG_{2b}$: Binding, 0.1 M sodium phosphate, pH 8.0; elution, 0.1 sodium citrate, pH 6.5. When a 2-iminobiotin-containing matrix, such as 2-iminobiotin agarose, is used as the support, the complex IgG and the chimeric protein can be eluted from the column with a solution of pH<4, such as 50 mM ammonium acetate, pH 3.5

A similar procedure can also be used to immobilize antigen. After the immobilization of the chimeric protein-antibody complexes, antigen molecules in a solution are applied to the column, so that the antigens bind to the antibodies immobilized on the gel matrix through the chimeric protein. Such immobilized antigens can be used to isolate the molecules having affinity for the antigen, such as cofactors, coenzymes, associated proteins, and substrates.

EXAMPLE 5

Conversion of Bivalent IgG to specific Multivalent IgG Capable of Conjugation to Biological Materials Containing Biotin This example describes a method to construct a multivalent antibody, which is capable of further conjugation to biological materials containing biotin, using the streptavidin-Protein A chimeric protein of this invention. Such multivalent antibodies can be easily constructed using the streptavidin-Protein A chimeric protein, which has four or more IgG binding sites per molecule.

The purified streptavidin-Protein A chimeric protein (50 µg, 0.4 nmol molecules, 1.6 nmol subunits) was mixed with 0.24 mg (1.6 nmol) human monoclonal antibody ($IgG_1$, $IgG_2$, or $IgG_4$), in which the molar ratio of chimeric protein subunit to antibody is 1. The antibody molecule binds to the Protein A moiety of the chimeric protein. Because one chimeric protein molecule consists of four identical subunits, each containing one or more IgG binding sites, the resulting chimeric protein-antibody conjugates contain four antibody molecules per conjugate molecule. Since each IgG molecule has two antigen binding sites (divalent), the chimeric protein-antibody complex containing four IgG molecules has eight antigen binding sites (octavalent). The number of antibody molecules per conjugate molecule can be controlled by mixing two molecules at an appropriate ratio. Because of the multiple, closely spaced antigen binding sites, such conjugates have a very high binding avidity for microorganisms or viruses, which are covered with identical subunits, as does IgM. In addition, such conjugates have four biotin binding sites per molecule, which allow stable conjugation or targeting of such conjugates to other biological materials containing biotin. For example, such conjugates containing antibodies to a cell surface protein can be easily immobilized on a solid support containing biotin, that serve as a tool for separation of target cells. I addition, the conjugates can also be used to target biotinylated materials to the target cells.

EXAMPLE 6

Construction of Bispecific Immune Reagents

This example describes a method to construct a bispecific antibody using the streptavidin-Protein A chimeric protein of this invention.

The purified streptavidin-Protein A chimeric protein (50 µg, 0.4 nmol molecules, 1.6 nmol subunits) is mixed with 60 µg (0.4 nmol) human monoclonal antibody ($IgG_1$, $IgG_2$, or $IgG_4$) to target X. The antibody molecule binds to the Protein A moiety of the streptavidin-Protein A chimeric protein. The resulting conjugates contain one antibody molecule per chimeric protein. The conjugates are mixed with 60 µg ( 0.4 nmol ) biotinylated human monoclonal antibody to target Y. The biotin molecule contained in the antibody binds to the streptavidin moiety of the chimeric protein. The resulting conjugates contains two antibody molecules, one is to target X and the other to target Y, bound to the Protein A and the streptavidin moieties of the chimeric protein, respectively. Thus this conjugate is bispecific; i.e., the molecule has the ability to bind two different antigens, X and Y. Such conjugates can be used as the stable cross-linker of two biological materials. For example, a conjugate containing two monoclonal antibodies, one is to a retroviral envelop glycoprotein such as gp70 and the other is to a specific cell surface protein of target cells, has the ability to specifically target a recombinant retrovirus to the surface of the target cells, that allows stable retroviral infection.

What is claimed is:

1. A purified recombinant streptavidin Protein A chimeric protein having a biotin-binding moiety and an antibody-binding moiety:

wherein said biotin-binding moiety of the chimeric protein binds specifically to one biotin molecule and the antibody-binding moiety of the chimeric protein binds specifically to one or two antibody molecules per subunit of said chimeric protein;

wherein a molecular mass of said chimeric protein is 31.4 kDa;

wherein said chimeric protein consists of 289 amino acids of which 12 are lysines, 3 are histidines, 7 are arginines, 7 are asparagines, 14 are aspartic acids, 33 are threonines, 22 are serines, 23 are glutamic acids, 14 are glutamines, 10 are prolines, 23 are glycines, 33 are alanines, 12 are valines, 4 are methionines, 9 are isoleucines, 21 are leucines, 9 are tyrosines, 10 are phenylalanines and 6 are tryptophanes; and wherein said chimeric protein is purified to at least 95% homogeneity by a denaturation-renaturation process followed by absorption on IgG Sepharose affinity column and by absorption on 2-iminobiotin agarose column;

wherein said denaturation-renaturation process is achieved by dialyzing the protein against guanidine hydrochloride and by subsequent removal of guanidine hydrochloride by dialysis;

wherein said protein is expressed from lysogen BL21(DE3) (pLysS) transformed with an expression vector pTSAPA-2 using a T7 RNA polymerase gene placed under the lac UV5 promoter;

wherein said expression vector pTSAPA-2 is constructed by inserting a part of the protein A gene into a polylinker sequence attached to the streptavidin gene; and wherein said part of the protein A inserted into a polylinker sequence represents coding sequences S, E, D and A of the protein A gene;

wherein said coding sequences are flanked by the $\Phi 10$ promoter and $T\Phi$ transcriptional terminator.

* * * * *